United States Patent [19]

Huguenel et al.

[11] Patent Number: 5,166,053
[45] Date of Patent: Nov. 24, 1992

[54] SPECIMEN ADEQUACY CONTROL FOR CHLAMYDIA ASSAYS

[75] Inventors: Edward D. Huguenel; William J. Knowles, both of Guilford, Conn.

[73] Assignee: Miles Inc., Elkhart, Ind.

[21] Appl. No.: 485,100

[22] Filed: Feb. 23, 1990

[51] Int. Cl.$^5$ ............................................. G01N 33/571
[52] U.S. Cl. ................................... 435/7.36; 435/7.92; 435/7.21; 435/259; 435/961; 435/967; 435/975; 435/973
[58] Field of Search ...................... 435/7.36, 7.21, 7.3, 435/7.92, 975, 967, 973, 961, 259; 436/510, 518

[56] References Cited

U.S. PATENT DOCUMENTS

| | | | |
|---|---|---|---|
| 4,814,275 | 3/1989 | Durda et al. | 435/7.23 |
| 4,920,045 | 4/1990 | Okuda et al. | 435/268 |
| 5,032,504 | 7/1991 | Mauck | 435/7.36 |

OTHER PUBLICATIONS

Friedman et al., "Correlation of Positive Rate of Microtrak Chlamydia Direct Specimen Test with Adequacy of Specimen Collection" Abstract C.19, Abstracts of the Annual meeting of ASM p. 331 (1986).

Fukushima et al. Abstract from "Immunohistochemical Observations of Keratins, Involucim and Apithelial Membrane Antigen in Urinary Bladder Carcinomas from Patients Infected with Schistosoma Haematobium", Virchows Archiv. A, 411(2):103-115 (1987).

Holmes, "The Chlamydic Epidemic" JAMA 245(17):1718-1723 (May 1, 1981).

Howard et al, "Correlation of the Percent of Positive Chlcomydia trachomatis Direct Fluorescent Antibody Detection Tests with the Adequacy of Specimen Collection", Diagn. Microbiol. Infect. Dis., 14:233-237 (1991).

Primary Examiner—Esther L. Kepplinger
Assistant Examiner—Carol E. Bidwell
Attorney, Agent, or Firm—Andrew L. Klawitter

[57] ABSTRACT

A method for determining the adequacy of a cervical or urethral test specimen collected for an immunological assay to detect the presence of *Chlamydia trachomatis*. Cells present in the specimen are disrupted to expose a substance present in or on *C. triachomatis* that is detectable by immunological reaction. In order to determine if the test specimen contains an adequate amount of the cervical or urethral cell type that serves as a host cell for *C. trachomatis*, the disrupted specimen is also reacted with an immunological reagent that produces a detectable complex upon specific binding with a substance present in or on columnar epithelial cells. The present invention therefore provides a control reaction that verifies the adequacy of the collected test specimen and thereby increases the confidence that a negative test result for the presence of Chlamydia indicates the absence of a *C. trachomatis* infection in the patient.

6 Claims, 1 Drawing Sheet

SPECIMEN ADEQUACY CONTROL FOR CHLAMYDIA ASSAYS

BACKGROUND OF THE INVENTION

The present invention relates to chemical assays, particularly immunoassays, for detecting *Chlamydia trachomatis*. More particularly, the invention concerns means for assessing the adequacy of a cellular test specimen to be assayed, specifically a cervical or urethral specimen.

*Chlamydia trachomatis* is a Gram-negative bacterium responsible for a number of disease manifestations in humans including trachoma, non-gonococcal urethritis, cervical infections and lymphogranuloma venereum. The development of extremely sensitive methods for the detection of Chlamydial infections is medically important since the organism is often harbored without obvious symptoms of infection.

Due to the obligate intracellular nature of its life cycle, the accurate detection of Chlamydia requires that the host cells in which the organism replicates be carefully sampled. In the case of genital, cervical and ocular infections, the participating host cells are the columnar epithelial cells [Kuo, C.-C. (1988) Host Response. In, *Microbiology of Chlamydia*, ed. A. L. Barron, CRC Press, Inc., Boca Raton, Fla., USA]. Columnar epithelial cells constitute a broad class of cell type found, among other places, in the mucus membranes lining the eye, urethral and portions of the female reproductive tract, including the cervix. The cells display a characteristic morphology that allow the trained individual to differentiate these cells from other cell types when observing a specimen under a microscope. Thus, the detection of *C. trachomatis* by staining under a microscope offers the opportunity to an individual performing the test to observe if an adequate number of columnar epithelial cells are present in the specimen.

Procedures for obtaining adequate sample collection for accurate testing for Chlamydia have been described in detail [Smith, T. F. and L. A. Weed (1983), Evaluation of Calcium Alginate-tipped Aluminum Swabs Transported in Culturettes Containing Ampules of 2-Sucrose Phosphate Medium for Recovery of *Chlamydia trachomatis*. Am. J. Clin. Pathol. 80:213-215; Embil, JA., Thiebaux, J., Manuel, F. R., Pereira, L. H. and S. MacDonald (1983), Sequential Cervical Specimens and the Isolation of *Chlamydia trachomatis*: Factors Affecting Detection. Sex. Trans. Dis. 10:62-66; and Singal, S. S., Reichman, R. C., Graman, P. S., Griesberger, C, Trupei, M. A. and Menegus, M. A. (1986), Isolation of *Chlamydia trachomatis* from Men with Urethritis: Relative Value of One vs. Two Swabs and Influence of Concomitant Gonococcal Infection. Sex. Trans. Dis. 13:50-52]. These procedures include specifications as to the composition of the swab to be used for the sampling, how the swab is actually deployed during the sampling process and how it is subsequently processed. Variations in any of these steps can, however, significantly alter the performance of the diagnostic assay. Furthermore, failure to collect a sample from the anatomical site at which these cells are located also can result in a false-negative test. Unfortunately, those responsible for collecting a proper sample, even highly-trained medical staff, do not always follow or appreciate the procedures specified for adequate collection of a specimen.

Recently, rapid immunoassay test devices have been devised which permit essentially untrained individuals to perform qualitatively determinations for the presence of a variety of clinically significant antigens and antibodies in biological specimens such as urine and swabs. Examples of such devices are described in U.S. Pat. Nos. 4,623,461 and 4,632,901 and in European Patent Publication Nos. 186,100 and 217,403. A rapid immunoassay test device specifically designed for the detection of Chlamydia is described in European Patent Publication No. 264,036.

The detection of Chlamydia by immunoassay is based on the binding of antigens present in Chlamydia cells by antibody raised to be specific to such antigens, and the ability to detect such binding, such as by the formation of an instrument readable or visually observable signal. In these assays, the test specimen is subjected to conditions to disrupt cellular material in order to expose detectable Chlamydia markers. In the process, therefore, the individual performing the test loses the ability to examine the disrupted sample for adequacy of epithelial cells collected. Currently, such immunoassays do not include any procedure or control to determine whether or not the sample taken from the patient is an adequate one, thus the risk of false-negative results can be significant. Because Chlamydia is present within infected cells, a negative test result can be due to the inadequacy of the sample collected rather than on the absence of Chlamydial infection.

SUMMARY OF THE INVENTION

The subject of the present invention is a method that provides the means for assessing the adequacy of the clinical material obtained from a patient for use in the detection of *Chlamydia trachomatis*, especially of genital and cervical infections. The method can be employed prior to cell culture diagnostic techniques, thus saving significant financial and human resources on testing of inadequate clinical samples, or can be performed simultaneously with rapid chemical tests, e.g., immunoassays, for Chlamydia. The method relies on the detection of columnar epithelial cell-specific markers, the presence of which in the clinical sample indicates the adequacy of a sample.

The specimen adequacy control of the present invention assures that the assayed specimen contains an adequate amount of the cell type that serves as the host cell for Chlamydia infection. The control increases confidence that a negative test result is due to the absence of a detectable amount of *C. trachomatis* in the specimen rather than a failure to collect an adequate sample from the patient.

In performing a chemical assay for the detection of Chlamydia in a cervical or urethral specimen, the collected specimen is treated to disrupt cells that are present and the resulting disrupted specimen mixture is contacted with a chemical reagent that provides a detectable response upon reaction with a substance in or on *C. trachomatis* cells. In accordance with the present invention, the disrupted specimen mixture is also contacted with a chemical reagent that produces a detectable response upon reaction with a substance present in or on columnar epithelial cells in order to determine if the specimen contained an adequate amount of infectable cells.

The present invention is particularly applicable to Chlamydia immunoassays wherein the presence of a Chlamydia antigen in the disrupted specimen mixture is detected by reaction with an antibody reagent, preferably an antibody reagent that is labeled to provide a visually observable color. A particularly useful specimen adequacy control reagent is an antibody reagent that binds to an antigen present in or on the surface of columnar epithelial cells, but which does not substantially bind to other antigens that might be present in the disrupted specimen mixture.

DESCRIPTION OF THE PREFERRED EMBODIMENTS

Figure 1:
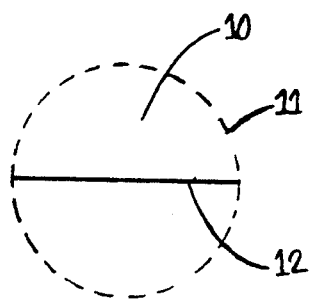
FIG. 1 shows the test device indicating a false negative test result where a dotted line represents a negative reaction and a solid line represents a positive reaction.

The chemical reaction, herein referred to as the control reaction, used to determine a substance, herein referred to as a marker, present in or on columnar epithelial cells is not critical provided that it produces a detectable response independent of the ability to microscopically observe the unique morphology of such cells. This is particularly important when applied to the immunoassay detection of Chlamydia where the cells, both host human cells and bacterial cells, in a test specimen are disrupted in order to expose Chlamydia antigens or other markers.

The control reaction can be responsive to any useful columnar epithelial cell marker, and will usually be, but is not intended to be limited to, biochemical in nature such as an immunochemical or enzymatic reaction which can confer a high degree of specificity and sensitivity to the control reaction. The control measurement relies on the detection of a columnar cell-specific characteristic not displayed by other cell types. It will normally be preferred to select a marker which is a unique antigen appearing on the surface of or internally in columnar epithelial cells. Such antigens can be proteins, carbohydrates, glycoproteins, lipoproteins, and the like, and will be readily detectable with antibody reagents following conventional techniques. While surface antigens specific for columnar epithelial cells are advantageous as markers in the present invention, of greater advantage is the measurement of a columnar cell-specific marker that is exposed only upon disruption or lysis of epithelial cells. Detection of such a marker would indicate not only that the required cell type is present, but also that cells have been lysed, an event that would liberate intracellular *C. trachomatis* and its markers for detection.

The preparation of antibody reagents specific to columnar epithelial cells can be readily accomplished by the skilled worker in the field. As used herein, the terms antibody and antibody reagent are intended to encompass any material, however obtained, which comprises an antibody combining site. Thus, included in the intended meaning of such terms are whole immunoglobulins as well as appropriate fragments or polyfunctionalized forms thereof. When in the form of whole immunoglobulin, it can belong to any of the known classes and subclasses such as IgG, IgM, and the like. Any fragment of any such immunoglobulin which retains a functional antibody combining site can also be employed, for instance, the fragments of IgG conventionally known as Fab, Fab', and F(ab')$_2$. In addition, aggregates, polymers, derivatives, conjugates, and hybrids of immunoglobulins or their fragments can also be used where appropriate.

The immunoglobulin source of the antibody reagent can be derived by any available technique. Most commonly, such techniques will be conventional polyclonal antiserum production or monoclonal antibody techniques. At the appropriate point in the generation of antibody, a host animal will be immunized with a material (conventionally referred to as an immunogen) in order to stimulate the production of antibodies of desired specificity and affinity by the immune system of the host. In order to generate a columnar epithelial cell antibody reagent, one skilled in the art will choose an appropriate immunogen. Such immunogen can be whole, intact, treated (e.g., denatured, reduced, oxidized, etc.) or untreated, columnar epithelial cells; a mixture obtained by disrupting or lysing such cells or a purified fraction or substance therefrom; a synthetically prepared peptide, polypeptide, carbohydrate, glycopeptide, lipopeptide, or the like, comprising an epitope specific to columnar epithelial cells; and so forth as is known in the art.

Monoclonal techniques will be particularly useful in the preparation of columnar epithelial cell marker-specific antibody reagents. For example, mice can be immunized with an immunogen as described above. Lymphocytes removed from immunized mice, pre-screened or not pre-screened for production of antibodies against or specific for columnar epithelial cells, are then fused under conventional conditions with murine myeloma cells, and the resulting hybridomas screened for secretion of antibodies of desired specificity, affinity, etc. For example, Ramaekers, et al [Ramaekers, F., Huysmans, A., Moesker, O., Kant, A., Jap, P., Herman, C. and P. Vooijs (1983), Monoclonal Antibody for Keratin Filaments, Specific for Glanular Epithelia and their Tumors. Lab. Invest. 49:353-361] describe a monoclonal antibody against a cytokeratin intermediate filament protein that is specific for glandular and columnar epithelial cells. This antibody does not react with other epithelial cell types, nor does it react with non-epithelial cells, and would find use in the present invention.

The control reagent of the present invention will be useful in conjunction with the performance of any chemical test for detecting Chlamydia, particularly where the assay specimen is subjected to conditions to disrupt cells in order to expose a detectable Chlamydia marker (a substance in or on Chlamydia cells that is characteristic of, or specific to, *C. trachomatis*). As in the case of the control reaction, the chemical reaction by which the Chlamydia marker is detected will usually be, but is not intended to be limited to, biochemical in nature such as an immunochemical or enzymatic reaction which can confer a high degree of specificity and sensitivity to the detection reaction. Since immunoassays are preferred, the Chlamydia marker will preferably be a unique antigen appearing on the surface of or internally in *C. trachomatis*. Such antigen can be a protein, carbohydrate, glycoprotein, lipoprotein, or the like, and will be readily detectable with antibody reagents following conventional techniques.

The following are given as just a few examples of immunoassay methods that are useful in the detection of Chlamydia. The sandwich immunoassay method involves the binding of a labeled antibody and an immobilized antibody to Chlamydia antigen. The resulting complex is separated from unbound labeled antibody and the label therein measured. In another method, Chlamydia antigen is adsorbed by nonspecific binding to a solid support and the adsorbed antigen detected by binding of labeled antibody.

The detectable responses produced by the test reaction and the control reaction, respectively, can be the same, similar, or different depending upon the needs or desirable characteristics of the assay. Such responses will of course be made to be observationally distinct in situations where the test and control reactions take place in the same location, e.g., in the same volume of test liquid or mixture, or in or on the same reaction zone of a solid support. Where two separate portions of the disrupted specimen mixture are contacted with the detection reagent and the control reagent, and the resulting responses are detected in separate locations, it is of course not necessary that the responses be distinct, but only that it be clear which response is the test response and which is the control response. Within these principles, a wide variety of assay method protocols and assay devices are possible.

In the performance of Chlamydia assays using the recently developed rapid immunoassay methods, typically a test device is used comprising a membrane or filter having an exposed area on its upper surface for receiving test liquids and reagents, and having its lower surface in contact with an absorbent material which serves to absorb liquids that flow through the membrane. The membrane or filter may or may not be incorporated with a test reagent, such as an anti-Chlamydia antibody in an immobilized form, but the final result of the assay is the formation of a localized area of color on the exposed surface of the membrane indicative of the presence of Chlamydia in the sample. A useful way to incorporate the subject control reaction in such devices is to localize the control reagent in a predetermined pattern distinct from the test area. Such control area can, in part, overlap or be contiguous with the test area in order that the combined responses produced by a positive test reaction and a positive control reaction provides a cooperative pattern of response which is readily distinguishable from the pattern of response produced by a positive control reaction only. Typical are the "±" patterns produced by currently marketed products, but essentially any useful pattern combination can be used.

Also, current rapid immunoassay test devices generally include a reagent control area or zone containing a reagent that interacts with the test reagents in order to assure that the lack of a positive test result is not due to a failure of the test reagents or an error in performing the test steps. Thus, it can be desirable to have distinct test, reagent, and sample adequacy control areas on the membrane surface. The choice of the respective patterns of such areas and the cooperative patterns that their responses make can be left to the desires and needs of the user of the test.

It will be most convenient that the test and control responses be visually observable in order that the test can be performed without need for analytical instrumentation and can be interpreted by a relatively untrained individual. The formation of color is particularly preferred and is readily obtained in the case of antigenic markers through the use of enzyme-labeled antibody reagents.

The present invention will now be illustrated, but is not intended to be limited, by the following example.

EXAMPLE

Preparation of Test Devices Having a Sample Adequacy Control Feature

Test devices as generally depicted in U.S. Pat. Nos. 4,623,461, 4,632,901 and 4,818,677 and in Published European Patent Publications Nos. 186,100 and 217,403 can be modified in accordance with the present invention to provide a visually read control area for specimen adequacy in a Chlamydia assay.

Figure 2:
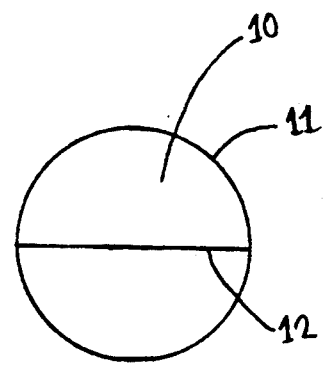
FIG. 2 shows the test device indicating a true negative test result.
Figure 3:
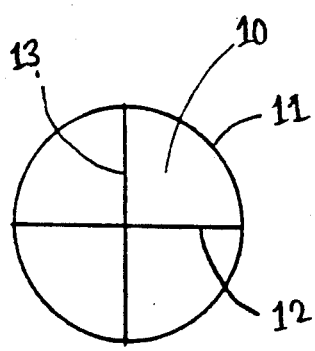
FIG. 3 shows the test device indicating a true positive test result.
Figure 4:
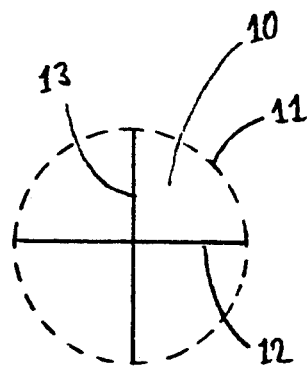
FIG. 4 shows the test device indicating an invalid test result.

The test devices or the assay reagents and protocols can be modified to provide the four possible assay results depicted in the drawings. With reference to FIG. 1, there is depicted a circular test surface area (10) comprising peripheral specimen control area (11) and horizontal reagent control area (12). The appearance of signal (e.g., color) in horizontal reagent control area (12) results from immobilization of a control reagent which interacts in cooperation with one or more components of the reagent system to indicate that such component(s) are working properly. For example, the immobilized control reagent can be an antibody directed against the antibody-enzyme conjugate used in the assay or a chlamydia-specific peptide that will react with the antibody-enzyme conjugate. As illustrated in FIGS. 2 & 3, the appearance of color in peripheral specimen control area (11) results from the immobilization of a chemical reagent composition of the present invention which interacts specifically with columnar epithelial cells. With reference to FIGS. 3 & 4, test area (10) also comprises vertical test area (13). The appearance of color in vertical test area (13) results from either (1) the immobilization of Chlamydia-specific antibody that can bind to Chlamydia antigen which in turn is or can be bound by labeled antibody, or (2) the limited application of the test mixture.

The interpretation of the four possible patterns that can result in the performance of assays is as follows:

FIG. 1 Indicates to the operator that the Chlamydia-specific assay reagents are working properly; however, the result is invalid since the peripheral circle sample control area (11) indicates a lack of sufficient columnar epithelial cells in the applied sample. This test result would therefore be a FALSE NEGATIVE and resampling of the patient would be required.

FIG. 2 Indicates that the Chlamydia-specific assay reagents are working properly and that the applied sample contained adequate columnar epithelial cells. This test result would therefore be a TRUE NEGATIVE for Chlamydia infection.

FIG. 3 Indicates that the Chlamydia-specific assay reagents are working properly, that the applied sample contained adequate columnar epithelial cells, and that the sample also contained Chlamydia. This test result therefore would be a TRUE POSITIVE for Chlamydia infection.

FIG. 4 Indicates the Chlamydia-specific assay reagents are working properly and gives a positive result for the presence of Chlamydia; however, the test result is invalid since the peripheral circle sample control area (11) indicates a lack of sufficient columnar epithelial cells in the applied sample. Thus, the detection of Chlamydia in the sample must be considered suspect. Repeat testing or culture confirmation would be required.

The following exemplary procedure uses the test device described above.

1. Clinical material (usually in the form of a cervical or urethral swab) is extracted in a solution containing detergent and other ingredients to release and expose both the Chlamydia antigens to be detected and the columnar epithelial cell-specific marker antigen.
2. Extracted material is mixed with (a) a first antibody reagent that is specific for a Chlamydia antigen and is labeled with an enzyme, (b) a second antibody reagent which is also specific for a Chlamydia antigen but which is unlabeled and bound to a filterable particle, and (c) a third antibody reagent that is specific for the columnar epithelial cell-specific marker antigen and that is labeled with the same enzyme as the first antibody reagent.
3. After a suitable incubation period, the test mixture is applied to the test device, the test mixture passing through the filter membrane.
4. After a wash step to remove nonspecific materials, a chromogenic enzyme substrate solution is applied to the test device and the resulting color pattern interpreted as described above.

The present invention has been particularly described and exemplified above. It is evident that other modifications and variations are possible without departing from the scope or spirit of the present invention.

What is claimed is:

1. In a method for detecting a *Chlamydia trachomatis* antigen present in a cervical or urethral specimen comprising treating a cervical or urethral specimen to disrupt cells that are present in the said specimen, contacting the resulting specimen mixture with a *C. trachomatis* antibody reagent which specifically binds to an antigen present in or on *C. trachomatis* to form a first complex and detecting the complex thus formed, wherein the improvement comprises reacting said disrupted specimen mixture with a columnar epithelial cell antibody reagent which specifically binds with an antigen present in or on the surface of columnar epithelial cells which serve as host cells for *C. trachomatis* and determining a second complex thus formed as an indication of the presence of an adequate amount of said columnar epithelial cells in said specimen mixture to allow for a valid test result.

2. The method of claim 1 wherein two separate portions of the disrupted specimen mixture are contacted with the *C. trachomatis* antibody reagent and the columnar epithelial cell antibody reagent, respectively, and the respective complexes are detected in the separate portions.

3. The method of claim 1 wherein the disrupted specimen is contacted with both the *C. trachomatis* antibody reagent and the columnar epithelial cell antibody reagent and the respective complexes are distinguishable in the resulting mixture.

4. A test kit for detecting *Chlamydia trachomatis* antigen in a cervical or urethral specimen comprising a *C. trachomatis* antibody reagent which specifically binds to an antigen present in or on *C. trachomatis*, wherein the collected specimen is treated to disrupt cells that are present and the resulting disrupted specimen mixture is contacted with the *C. trachomatis* antibody reagent to form a first complex, and a columnar epithelial cell antibody reagent which specifically binds with an antigen present in or on the surface of columnar epithelial cells to form a second complex, whereby said specimen mixture formed by treatment of said specimen to disrupt cells present therein is tested for the presence of an adequate amount of columnar epithelial cells that serve as host cells for *C. trachomatis* as an indication of the presence of an adequate amount of said columnar epithelial cells in said specimen mixture to allow for a valid test result.

5. The test kit of claim 4 comprising separate reaction sites for contact between the disrupted specimen and said *C. trachomatis* antibody reagent and said columnar epithelial cell antibody reagent, respectively.

6. The test kit of claim 4 wherein the specific binding of said *C. trachomatis* antibody reagent to its antigen is distinguishable from the specific binding of said columnar epithelial cell antibody reagent with its antigen.

* * * * *